US008668875B2

(12) United States Patent
Murakami

(10) Patent No.: US 8,668,875 B2
(45) Date of Patent: Mar. 11, 2014

(54) STIRRING DEVICE AND AN ANALYZING DEVICE

(75) Inventor: Miyuki Murakami, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/122,384

(22) PCT Filed: Mar. 23, 2009

(86) PCT No.: PCT/JP2009/055632
§ 371 (c)(1),
(2), (4) Date: Apr. 1, 2011

(87) PCT Pub. No.: WO2010/038494
PCT Pub. Date: Apr. 8, 2010

(65) Prior Publication Data
US 2011/0176964 A1   Jul. 21, 2011

(30) Foreign Application Priority Data

Oct. 3, 2008 (JP) ................................. 2008-259084

(51) Int. Cl.
*B06B 1/00* (2006.01)
(52) U.S. Cl.
USPC ............................ 422/127; 422/128; 422/224
(58) Field of Classification Search
USPC ........... 422/127, 224, 20, 21; 331/40; 73/641, 73/642, 632, 861.23
See application file for complete search history.

(56) References Cited

U.S. PATENT DOCUMENTS

2003/0166260 A1*   9/2003   Katou et al. ............... 435/287.1

FOREIGN PATENT DOCUMENTS

| EP | 1 340 535 A | 9/2003 |
| EP | 1 947 462 A | 7/2008 |
| JP | 2003-254981 A | 9/2003 |
| JP | 2007-108062 A | 4/2007 |
| WO | WO 2007-043261 A1 | 4/2007 |

* cited by examiner

*Primary Examiner* — Natalia Levkovich
(74) *Attorney, Agent, or Firm* — Kilpatrick Townsend & Stockton LLP

(57) ABSTRACT

A stirring device and an analyzing device for stirring a liquid retained in a vessel with sound wave. The Stirring device (20) comprises: a surface acoustic wave element (24) having sound generation section (24b, 24c) located on a piezoelectric substrate (24a) wherein the sound generation sections are electrically connected in parallel, and center frequencies of respective fundamental waves of the sound generation sections differ from each other, respective resonant frequency bands of the sound generation section are partially overlapped with each other, and origins of acoustic stream caused by sound wave radiated to the vessel from different sound generation section are located alternately; and a drive control section (21) for controlling a frequency of drive signal input to the surface acoustic wave element so that at least two sound generation sections of the plurality of sound generation sections generate sound wave simultaneously.

5 Claims, 18 Drawing Sheets

FIG. 13
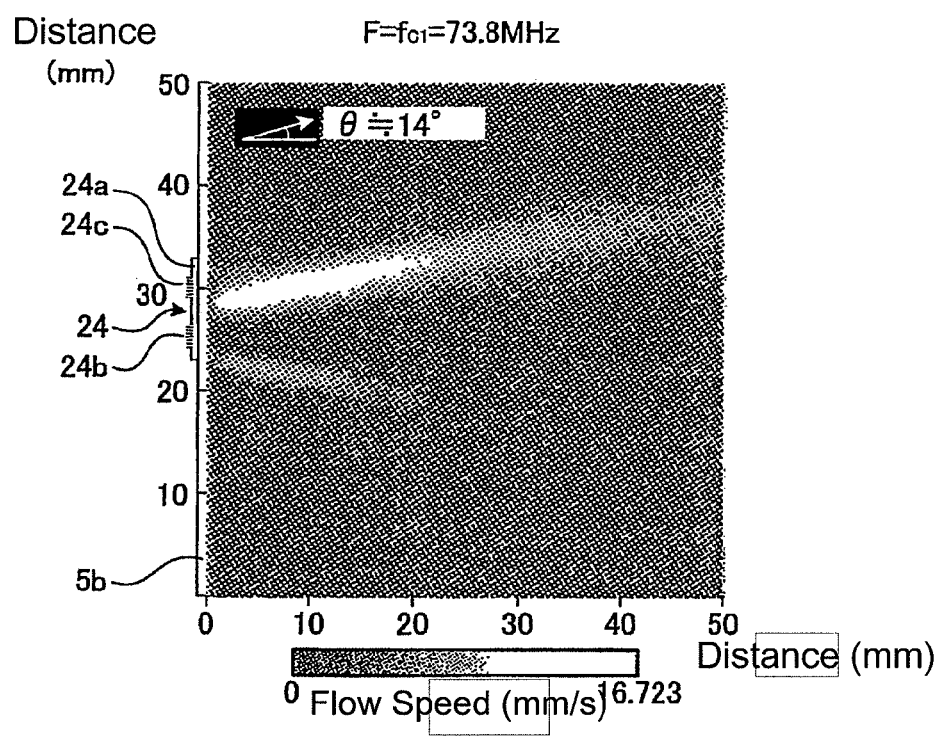
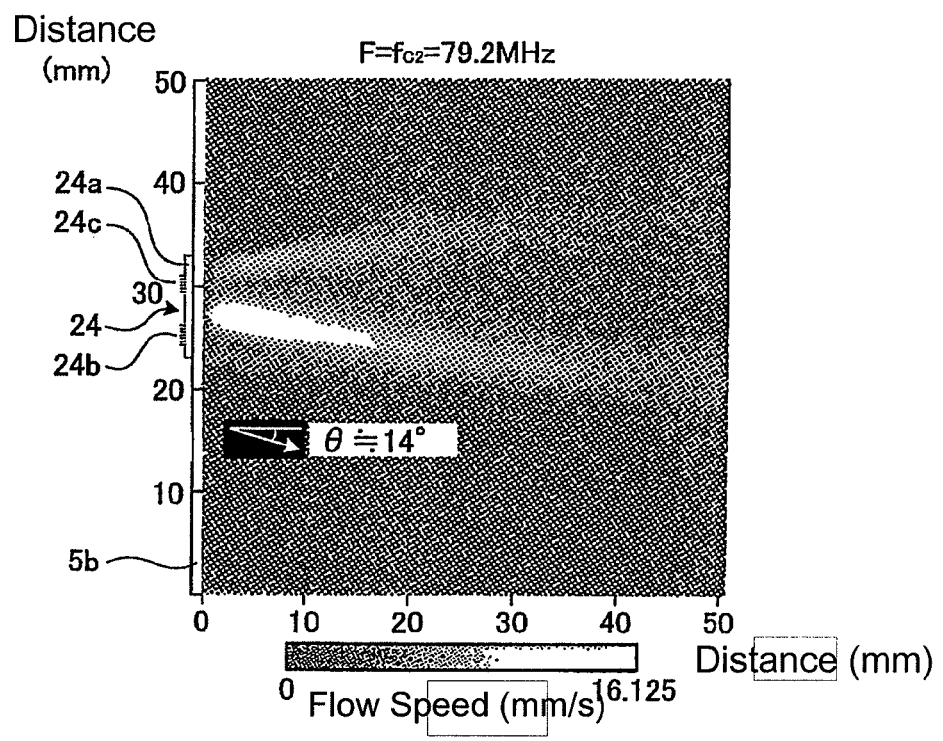

STIRRING DEVICE AND AN ANALYZING DEVICE

CROSS-REFERENCE TO RELATED APPLICATION

This application is a National Stage of International Application No. PCT/JP2009/055632, filed Mar. 23, 2009, which claims the benefit of priority to Japanese Application No. 2008-259084, filed Oct. 3, 2008, the disclosures of each are herein incorporated by reference.

TECHNICAL FIELD

The present invention relates to a stirring device and an analyzing device.

BACKGROUND ART

Conventionally, in an example of a stirring device for stirring a liquid retained in a vessel with sound wave, a sound wave generation means having a plurality of sound generation sections each having a different center frequency, and the stirring device changes a drive frequency to switch the sound generation section which emits the sound wave to a specific sound generation section among the plurality of sound generation sections in time sharing to stir the liquid (for example, refer to Patent Document 1).

Patent Document 1: Japanese Laid-Open Publication No. 2007-108062

DISCLOSURE OF THE INVENTION

Problems to be Solved by the Invention

Since the stirring device disclosed in the Patent Document 1 performs a stirring by changing a plurality of sound generation sections in time-sharing, only partial sound generation sections of the plurality of sound generation sections are used; therefore, a problem exists that much time is required for a stirring.

The present invention is made in view of the above, the purpose of which is to provide a stirring device and analyzing device capable of reducing time required for a stirring.

Means for Solving Problems

In order to solve the problem and achieve the purpose mentioned above, the stirring device of the present invention is a stirring device for stirring a liquid retained in a vessel with sound waves characterized by comprising:

a sound wave generation means having sound generation sections located on a piezoelectric substrate, the sound generation means being configured so that a plurality of the sound generation sections are electrically connected in parallel, center frequencies of respective fundamental waves of sound generation sections differ from each other, respective resonant frequency bands of the sound generation sections are partially overlapped with each other, and the origins of an acoustic stream are caused by sound waves radiated to the vessel from different sound generation sections are located alternately; and a drive control means for controlling a frequency of a drive signal input to the sound wave generation means so that at least two sound generation sections of the plurality of sound generation sections generate sound waves simultaneously.

In addition, the plurality of sound generation sections in the stirring device of the present invention are characterized in that a ratio of response intensity of vibration to an electrical input signal of the respective sound generation sections is varied according to a frequency of the drive signal.

In addition, the plurality of sound generation sections in the stirring device of the present invention are characterized in that the sound generation section which generates sound wave is switched according to a frequency of the drive signal.

In addition, in the stirring device of the present invention, the drive control means is characterized by varying a frequency of the drive signal input to the sound wave generation means based on an analysis item of the liquid and information of property or a liquid volume of the liquid.

In addition, in the stirring device of the present invention, the drive control means is characterized by varying a frequency of the drive signal to cause an acoustic stream which rotates in the liquid.

In addition, in order to solve the problem and to achieve the purpose mentioned above, the analyzing device of the present invention is an analyzing device which stirs a liquid sample containing analyte and reagent retained in a vessel to be reacted to analyze a reacted liquid, characterized by comprising the stirring device.

Effect of the Invention

Since the stirring device of the present invention comprises a sound wave generation means having sound generation sections located on a piezoelectric substrate, the sound wave generation means being configured so that a plurality of the sound generation sections are electrically connected in parallel, the center frequencies of respective fundamental waves of sound generation sections differ from each other, the respective resonant frequency bands of sound generation section are partially overlapped with each other, and the origins of acoustic stream caused by sound waves radiated to the vessel from different sound generation sections are located alternately; and a drive control means for controlling a frequency of drive signal input to the sound wave generation means so that at least two sound generation sections of the plurality of sound generation sections generate sound wave simultaneously and since the analyzing device of the present invention comprises the stirring device, a mode of an acoustic stream caused in a liquid stirred by sound waves simultaneously generated from at least two sound generation sections becomes diversified thereby to attain the effect of reducing time required for a stirring.

BRIEF DESCRIPTION OF THE DRAWINGS

FIG. 13 is a profile visualizing flow speed distribution of acoustic streams generated in the case that respective sound generation sections having frequency characteristic shown in FIG. 12 are driven at respective center frequencies.

DESCRIPTION OF REFERENCE NUMERALS

Figure 1:
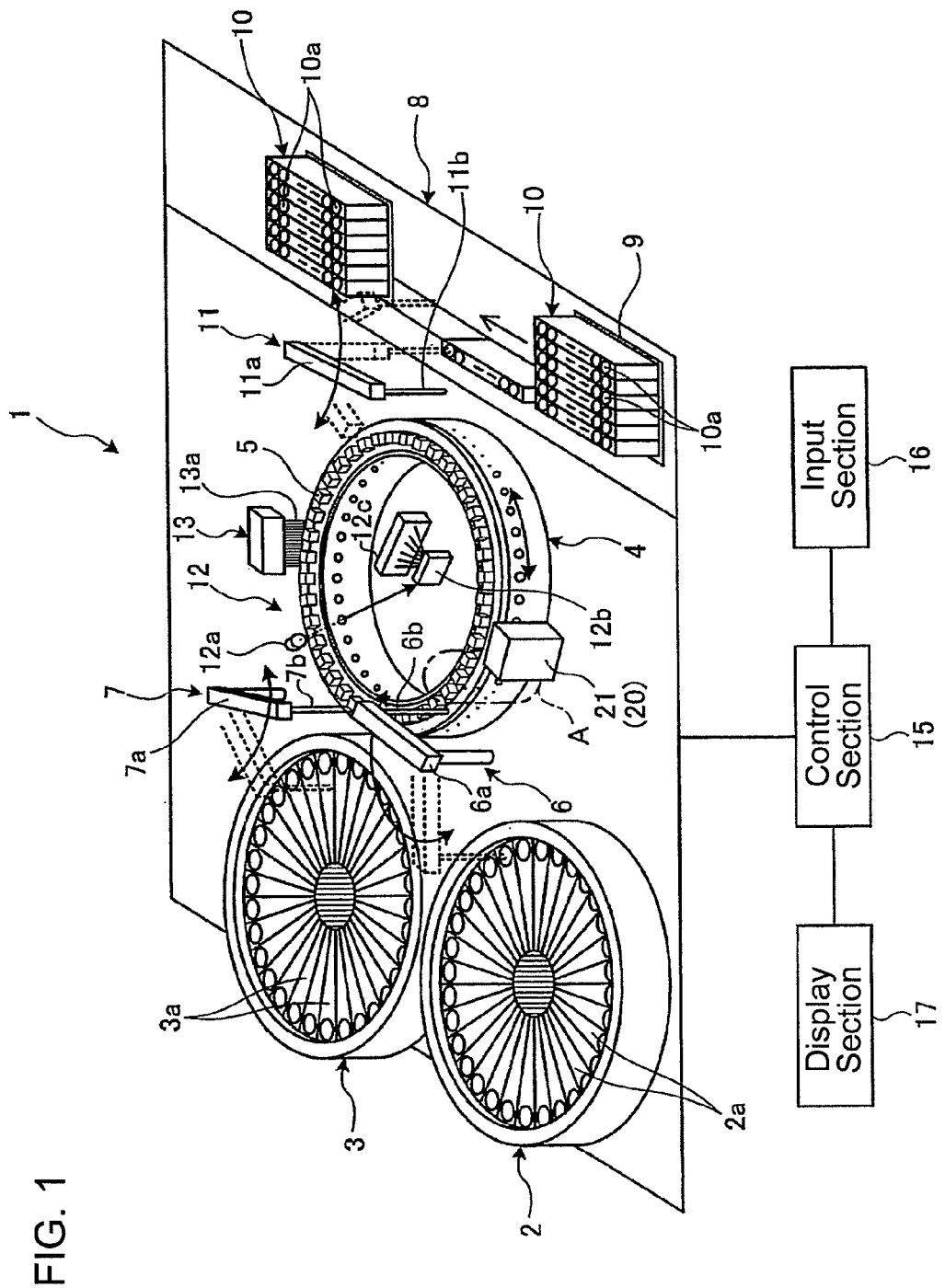
FIG. 1 is a skeleton configuration diagram of an automatic analyzing device comprising a stirring device.

1 Automatic analyzing device
2, 3 Reagent table
4 Cuvette wheel
5 Reaction vessel
6, 7 Reagent dispensing mechanism
8 Analyte vessel transfer mechanism
9 Feeder
10 Rack
11 Analyte dispensing mechanism
12 Analysis optical system
13 Cleaning mechanism
15 Control section
16 Input section
17 Display section
20 Stirring device
21 Drive control section
22 Signal generator
23 Driving control circuit
24 Surface acoustic wave element
24a Piezoelectric substrate
24b, 24c Sound generation section
24d Sound generation section
24e Input terminal
24f Bus bar
240b, 240c Comb-shaped electrode (IDT)
240d Comb-shaped electrode (IDT)

BEST MODE FOR CARRYING OUT THE INVENTION

Figure 2:
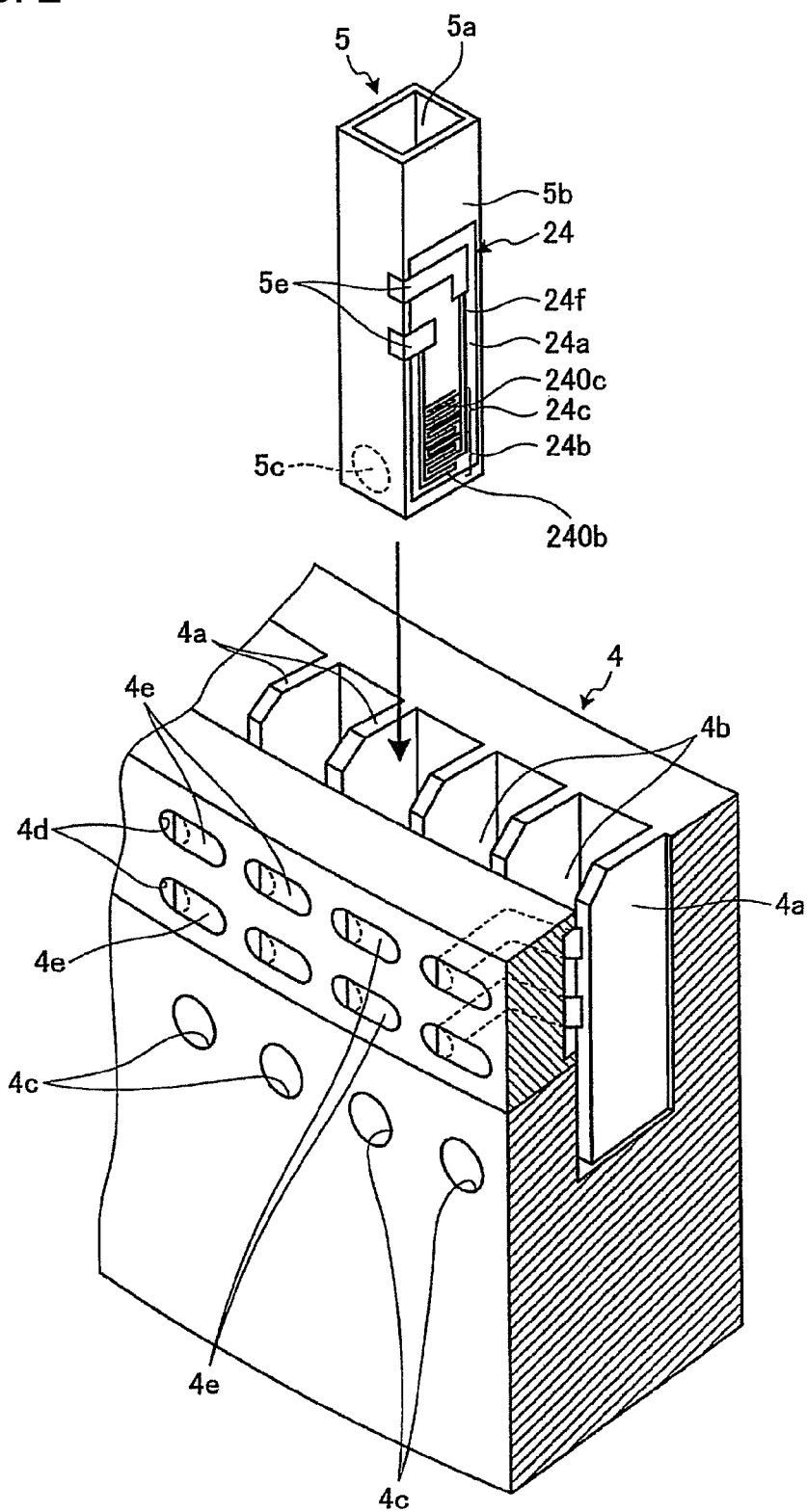
FIG. 2 is a perspective view depicting an enlarged portion A of a cuvette wheel configuring the automatic analyzing device shown in FIG. 1, and apart of an enlarged portion A is depicted with cross section.
Figure 3:
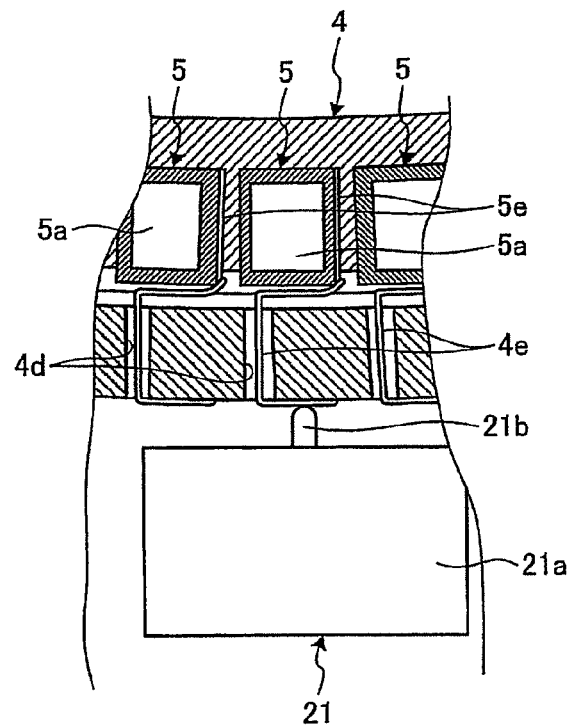
FIG. 3 is a cross sectional plan view which horizontally cuts the cuvette wheel containing a reaction vessel at the position of a wheel electrode.
Figure 4:
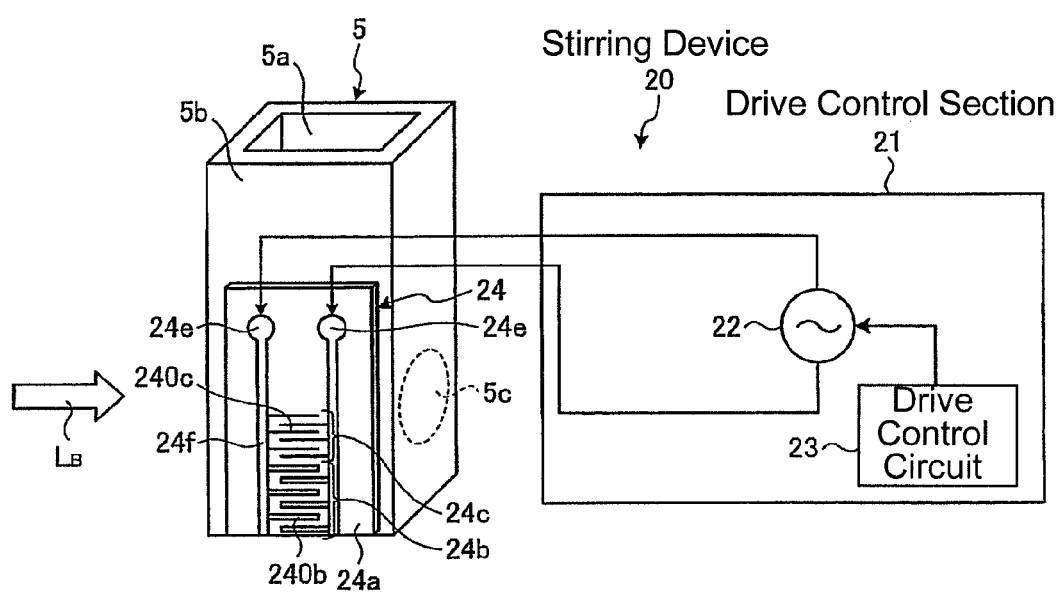
FIG. 4 is a block diagram depicting a skeleton configuration of a stirring device with perspective view of a reaction vessel.

In the following, embodiments relating to a stirring device and an analyzing device of the present invention will be explained in detail with reference to the drawings. FIG. 1 is a skeleton configuration diagram of an automatic analyzing device comprising a stirring device. FIG. 2 is a perspective view depicting an enlarged portion A of a cuvette wheel configuring the automatic analyzing device shown in FIG. 1, and a part of an enlarged portion A is depicted with cross section. FIG. 3 is a cross sectional plan view which horizontally cuts the cuvette wheel containing a reaction vessel at the position of a wheel electrode. FIG. 4 is a block diagram depicting a skeleton configuration of a stirring device with perspective view of a reaction vessel.

The automatic analyzing device 1 comprises reagent tables 2 and 3, a cuvette wheel 4, an analyte vessel transfer mechanism 8, analysis optical system 12, a cleaning mechanism 13, a control section 15 and a stirring device 20 as shown in FIG. 1 and FIG. 2.

The reagent tables 2 and 3 retain a plurality of reagent vessels 2a and 3a each located in a circumferential direction as shown in FIG. 1 and transfer the reagent vessels 2a and 3a in the circumferential direction rotated by a drive means.

As shown in FIG. 1 and FIG. 2, the cuvette wheel 4 has a plurality of holders 4b formed in the circumferential direction for arranging a reaction vessel 5 by a plurality of partition plates 4a which are formed in the circumferential direction, and the cuvette wheel 4 is rotated in the direction indicated with an arrow by a driving means (not shown) so as to convey the reaction vessel 5. As shown in FIG. 2, photometry holes 4c are formed at the position of the cuvette wheel 4 corresponding to the lower part of the respective holders 4b in the radius direction. Wheel electrodes 4e are mounted by utilizing each of two vertically arranged insertion holes 4d formed above the photometry holes 4c. As shown in FIG. 2 and FIG. 3, one end of the wheel electrode 4e extending from the insertion hole 4d is bent to be in contact with the outer face of the cuvette wheel 4, while the other end extending from the insertion hole 4d is bent to be arranged in the vicinity of the inner face of the holder 4b, thereby holding the reaction vessel 5 arranged in the holder 4b with a spring force. A reagent is dispensed into the reaction vessel 5 from the reagent vessels 2a and 3a of the reagent tables 2 and 3 by the reagent dispensing mechanisms 6 and 7 arranged in the vicinity. Here, the reagent dispensing mechanisms 6 and 7 comprise probes 6b and 7b that dispense the reagent to arms 6a and 7a that pivot in the horizontal plane in the direction shown by an arrow, and have cleaning means for cleaning the probes 6b and 7b with cleaning water.

On the other hand, the reaction vessel 5 is made of an optically transparent material. As shown in FIG. 2, the reaction vessel 5 is a cuvette having a square cylindrical shape and having an opening 5a in the upper portion. A surface acoustic wave element 24 is mounted at the sidewall 5b of the reaction vessel 5 as a sound wave generation means and electrode pads 5e that are connected to a set of input terminals 24e of the surface acoustic wave element 24 are mounted on the reaction vessel. The reaction vessel 5 is made of a material that transmits 80% or more of light of the analytical light emitted from an analysis optical system 12 which will be described later, for example, a glass containing a heat-resistant glass, a synthetic resin such as ring olefin or polystyrene and the like are used. The portion of the reaction vessel 5 encircled by a dotted line at the lower part thereof adjacent to the portion where the surface acoustic wave element 24 is mounted is used as a window 5c for photometry which allows the analytical light to transmit. When the reaction vessel 5 is used, and the reaction vessel 5 is set to the holder 4b with the surface acoustic wave element 24 facing the partition plate 4a. Thus, as shown in FIG. 3, each of the electrode pads 5e of the reaction vessel 5 contacts with the corresponding wheel electrode 4e. The electrode pads 5e are configured to be integral with the surface acoustic wave element 24.

As shown in FIG. 1, the analyte vessel transfer mechanism 8 is transfer means for transferring, one by one, a plurality of racks 10 arranged to a feeder 9 along the direction indicated by the arrow, wherein the racks 10 are transferred as advanced step by step. The rack 10 holds a plurality of analyte vessels 10a containing an analyte. Every time the advance of the rack 10 transferred by the analyte vessel transfer mechanism 8 is stopped, the analyte is dispensed into respective reaction vessels 5 by an analyte dispensing mechanism 11 having an arm 11a that is horizontally pivoted and a probe 11b. Therefore, the analyte dispensing mechanism 11 has cleaning means for cleaning the probe 11b with cleaning water.

The analysis optical system 12 emits an analytical light for analyzing the liquid sample in the reaction vessel 5, obtained by the reaction of the reagent and the analyte. As shown in FIG. 1, the analysis optical system 12 has a light-emitting section 12a, a spectroscopy section 12b, and a light-receiving section 12c. The analytical light emitted from the light-emitting section 12a transmits the liquid sample in the reaction vessel 5 and is received by the light-receiving section 12c provided at the position opposite to the spectroscopy section 12b. The light-receiving section 12c is connected to the control section 15.

The cleaning mechanism 13 sucks the liquid sample in the reaction vessel 5 with a nozzle 13a for discharging the same, and then, repeatedly injects and sucks cleaning liquid such as a detergent or cleaning water by the nozzle 13a, whereby the reaction vessel 5 in which the analysis by the analysis optical system 12 is completed is cleaned.

The control section 15 controls the operation of each section of the automatic analyzing device 1, and analyzes the component or concentration of the analyte based on the absorbance of the liquid sample in the reaction vessel 5 according to the quantity of the light emitted from the light-emitting section 12a and the quantity of the light received by the light-receiving section 12c. For example, a microcomputer or the like is used for the control section 15. The control unit 15 is connected to an input section 16 and a display section 17 as shown in FIG. 1. The input section 16 is a portion for inputting inspection items and the like to the control section 15. For example, a keyboard or mouse and the like are used for the input section 16. The input section 16 is also used for the operation of switching the frequency of a drive signal input to the surface acoustic wave element 24 of the stirring device 20. The display section 17 displays the content of the analysis or alarm. A display panel and the like are used for the display unit 17.

As shown in FIG. 4, the stirring device 20 has the drive control section 21 and the surface acoustic wave element 24 as a sound wave generation means.

The drive control section 21 is a drive control section that changes the frequency of the drive signal input to the surface acoustic wave element 24 based on the information input from the input section 16 via the control section 15, such as analysis items of the liquid, properties or amounts of the liquid and the like, to switch the position of a sound generation section which generates a sound wave. At this time, the drive control section 21 controls the frequency of drive signal within resonant frequency bands common to a plurality of sound generation sections 24b and 24c so that they simultaneously generate sound waves with different frequencies. The drive control section 21 is arranged so as to face the cuvette wheel 4 at the outer periphery of the cuvette wheel 4 (refer to FIG. 1) and has a brush-like contactor 21b (refer to FIG. 3) provided to a housing 21a, as well as a signal generator 22 and a drive control circuit 23 within the housing 21a. The contactor 21b is provided at the housing 21a opposite to the two wheel electrodes 4e, wherein the contactor 21a contacts with the wheel electrodes 4e when the cuvette wheel 4 stops, so that the drive control section 21 and the surface acoustic wave element 24 of the reaction vessel 5 are electrically connected.

The signal generator 22 has an oscillation circuit that can change the oscillation frequency based on the control signal input from the drive control circuit 23, and inputs a high-frequency drive signal of several MHz to several hundred MHz to the surface acoustic wave element 24. Electronic control means (ECU) having a memory and a timer incorporated therein is used for the drive control circuit 23. The drive control circuit 23 controls the operation of the signal generator 22 based on the control signal input from the input section 16 via the control section 15, thereby controlling the voltage or current of the drive signal output to the surface acoustic wave element 24 from the signal generator 22. The drive control circuit 23 controls, for example, the characteristic (frequency, intensity, phase, characteristic of a wave), waveform (sine wave, triangular wave, rectangular wave, burst wave and the like), modulation (amplitude modulation, frequency modulation), or the like of the sound wave emitted from the surface acoustic wave element 24 by controlling the operation of the signal generator 22. In addition, the drive control circuit 23 can vary the frequency of the high-frequency signal oscillated by the signal generator 22 in accordance with the incorporated timer.

As shown in FIG. 4, the surface acoustic wave element 24 has sound generation sections 24b and 24c spaced apart, which are composed of comb-shaped electrodes (IDT) 240b and 240c, on the surface of a piezoelectric substrate 24a, and the sound generation sections 24b and 24c and a set of input terminals 24e are connected by the bus bar 24f. The surface acoustic wave element 24 is attached to the sidewall 5b of the reaction vessel 5 via an acoustic matching layer such as epoxy resin or the like with a longitudinal direction of the piezoelectric substrate 24a directed to a longitudinal direction of the sidewall 5b. The sound generation sections 24b and 24c convert a drive signal input from the drive control section 21 to a surface acoustic wave (sound wave). In addition, the input terminals 24e of the surface acoustic wave element 24 are connected to single drive control section 21 by the contactor 21b which contacts to the wheel electrodes 4e.

Figure 5:
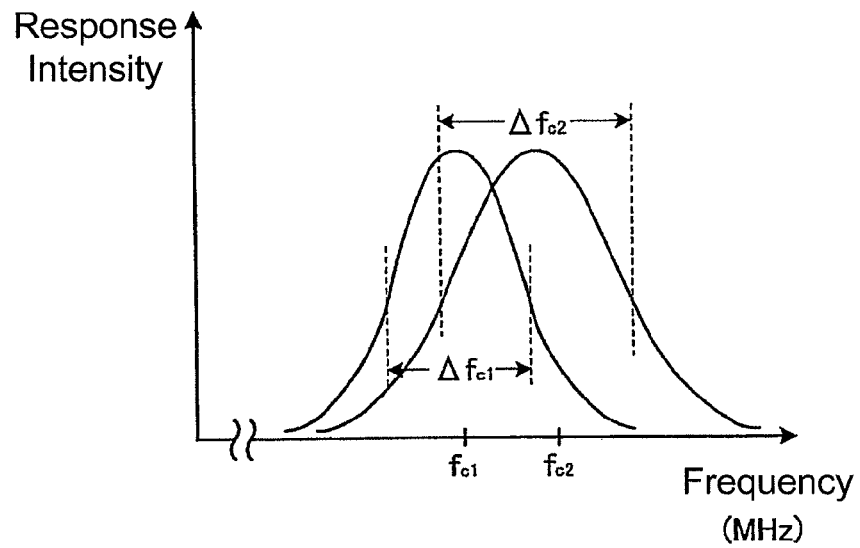
FIG. 5 is a graph showing resonant frequency bands of sound generation sections a part of which are overlapped.
Figure 6:
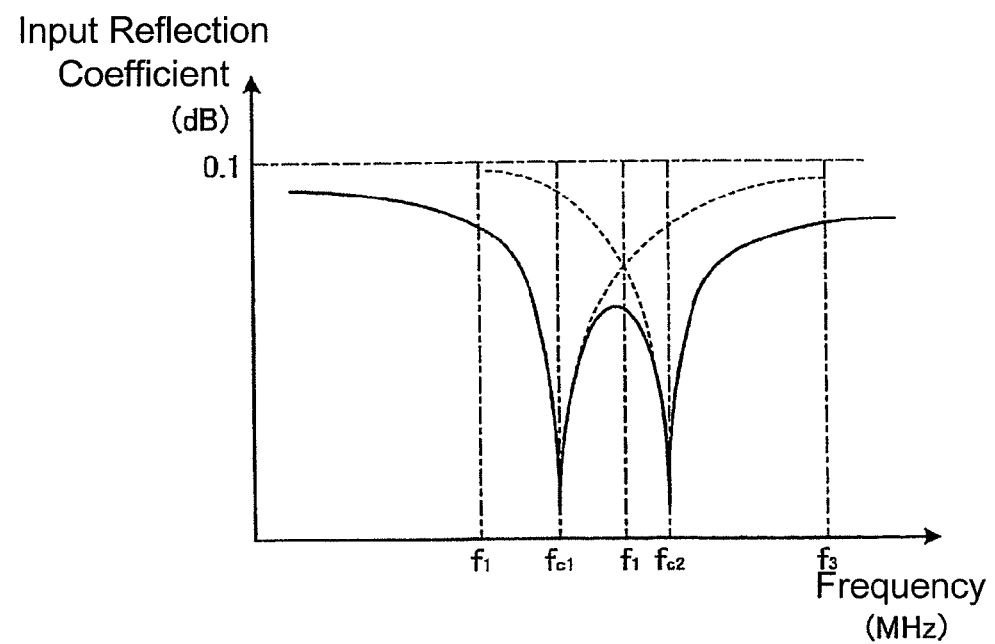
FIG. 6 is a frequency characteristic chart relating to center frequencies and input reflection coefficients which sound generation section of a surface acoustic wave element configuring the stirring device of FIG. 4.

In this case, a part of resonant frequency band of the sound generation section 24b and 24c are overlapped. That is, as shown in FIG. 5, a center frequency of a fundamental wave of the sound generation section 24b is fc1 and a center frequency of a fundamental wave of the sound generation section 24c is fc2 (fc1<fc2) (MHz), and when defining a resonant frequency band with a half-width $\Delta fc1$ or $\Delta fc2$ at which a response intensity value of $-3$ dB of response intensity of oscillation for electrical input signal at respective center frequencies, part of the resonant frequencies are overlapped. In addition, concerning an input reflection coefficient (dB), the sound generation sections 24b and 24c have frequency characteristics separately shown with dotted line in FIG. 6, and a solid line shows a frequency characteristic in combination of the two frequency characteristics. Furthermore, the sound generation sections 24b and 24c are formed so that origins of acoustic stream are arranged alternately. Regarding this point, it is described later.

Here, as the piezoelectric substrate 24a, for example, the crystal of lithium niobate (LiNbO3) of Y cut Z propagation (YZ) can be used. In addition, the sound generation sections 24b and 24c are formed on the piezoelectric substrate 24a in conjunction with input terminals 24e or bus bar 24f by the photolithography technology. In addition, the surface acoustic wave element 24 may be attached to the reaction vessel 5 in separable/contactable manner via an acoustic matching layer such as liquid or gel and the like. In the drawings depicting the surface acoustic wave element explained below including the surface acoustic wave element 24 shown in FIG. 4, the line width or pitch or position on the piezoelectric substrate 24a of the comb-shaped electrodes is not always correctly illustrated, because the main purpose of the drawings is to show a schematic structure.

In the automatic analyzing device 1 thus configured, the reagent dispensing mechanisms 6 and 7 successively dispense the reagent from the reagent vessels 2a and 3a into the plurality of reaction vessels 5 conveyed along the circumferential direction by the rotating cuvette wheel 4. The analyte is successively dispensed by the analyte dispensing mechanism 11 from the plurality of analyte vessels 10a retained at the rack 10 into the reaction vessels 5 to which the reagent has been dispensed. Consequently, every time the cuvette wheel 4 stops, the contactor 21b contacts with the wheel electrode 4e, so that the drive control section 21 and the surface acoustic wave element 24 of the reaction vessel 5 are electrically connected. Therefore, the dispensed reagent and the analyte in the reaction vessel 5 are successively stirred to be reacted by the stirring device 20.

In the automatic analyzing device 1, the amount of the analyte is generally smaller than the amount of the reagent; therefore, the analyte in a small amount dispensed into the reaction vessel 5 are caught by the reagent in a large amount due to a series of flow caused by the stirring in the liquid, whereby the reaction of the analyte and the reagent is accelerated. The reaction solution obtained by the reaction of the analyte and the reagent as described above passes through the analysis optical system 12 when the cuvette wheel 4 rotates again, and as shown in FIG. 4, a light beam LB emitted from the light-emitting section 12a transmits the reaction solution. In this case, the reaction solution of the reagent and the analyte in the reaction vessel 5 is subject to photometry by the light-receiving section 12c, whereby the component, concentration or the like is analyzed by the control section 15. Then the reaction vessel 5 after completing the analysis is cleaned by the cleaning mechanism 13, and used again for the analysis of the analyte.

In the automatic analyzing device 1, the drive control section 21 inputs the drive signal to the input terminals 24e via the contactor 21b based on the control signal previously input from the input section 16 via the control unit 15, when the cuvette wheel 4 stops. Thus, the sound generation section 24b or the sound generation section 24c of the surface acoustic wave element 24 is driven in accordance with the frequency of the input drive signal so as to induce a surface acoustic wave (bulk wave). The induced surface acoustic wave (bulk wave) is propagated from the acoustic matching layer into the sidewall 5b of the reaction vessel 5, and leaks into the liquid sample an acoustic impedance of which is close to that of the surface acoustic wave. As a result, two streams toward the diagonally upward direction and toward the diagonally downward direction with the origin corresponding to the sound generation section 24b or the sound generation section 24c in the liquid sample are produced in the reaction vessel 5, whereby the dispensed reagent and the analyte are stirred by these two streams.

Figure 7:
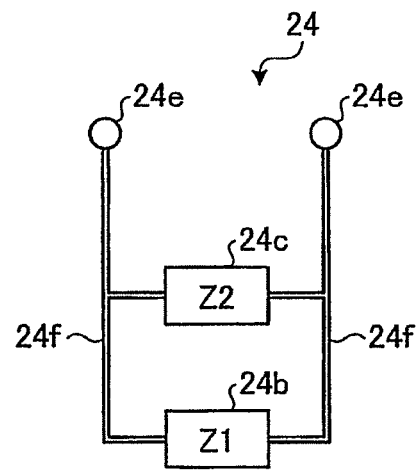
FIG. 7 is an equivalent circuit diagram of the surface acoustic wave element configuring the stirring device of FIG. 4.
Figure 8:
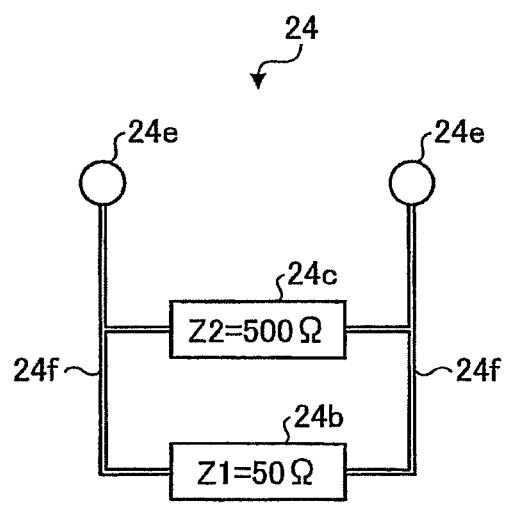
FIG. 8 is an equivalent circuit figure in the case that the surface acoustic wave element in FIG. 7 is driven at the center frequency of one sound generation section.

The surface acoustic wave element 24 is designed such that the electric impedance at the center frequency of the respective sound generation sections 24b and 24c are set to 50 ohms that is the same as the electric impedance of an external electric system. At this time, the equivalent circuit of the surface acoustic wave element 24 is as shown in FIG. 7 with the impedances of the sound generation sections 24b and 24c defined as Z1 and Z2 respectively. Therefore, when the drive control section 21 inputs the drive signal with the frequency fc1 to the surface acoustic wave element 24, for example, the electric impedance of the sound generation section 24b becomes Z1=50 ohms, while the electric impedance of the sound generation section 24c becomes Z2=500 ohms as shown in FIG. 8. For this reason, the sound generation section 24b of the surface acoustic wave element 24 is strongly excited, while the sound generation section 24c of the surface acoustic wave element 24 is weakly excited.

In this case, the sound wave generated by the excited sound wave generation sections 24b and 24c is propagated on the piezoelectric substrate 24a and the side wall 5b of the reaction vessel 5 so as to be mode-converted to a longitudinal wave at solid-liquid interface between the side wall 5b and the liquid sample Ls contained in the reaction vessel 5, then emitted into the liquid sample Ls. An acoustic stream is generated as the emitted longitudinal wave propagates in the liquid sample. In this case, the sound generation sections 24b and 24c are formed so as to alternately arrange the origins of acoustic stream, and the acoustic stream due to the sound wave W1 generated by the excited sound generation section 24b is expressed as S11 and the acoustic stream due to the sound wave W2 generated by the excited sound generation section 24c is expressed as S12.

In this case, as depicted, the acoustic stream S11 which is produced toward the diagonally upward direction in the liquid sample Ls of the acoustic stream S11 due to the sound wave W1 generated by the excited sound generation section 24b is produced at a location interleaved with two acoustic streams S12 produced toward the diagonally upward direction and toward the diagonally downward direction in the liquid sample Ls due to the sound wave W2 generated by the excited sound generation section 24c. Due to the above, two acoustic streams S12 are integrated with the acoustic stream S11 caused toward the diagonally upward right direction to form an acoustic stream S1 with large cross section and high flow speed. While the acoustic stream S11 produced toward the diagonally downward right direction in the liquid sample Ls due to the sound wave W1 generated by the excited sound generation section 24b is an independent flow which has smaller cross section and lower flow speed compared with the acoustic stream S1. Therefore, when the surface acoustic wave element 24 is driven with drive frequency F=fc1, macroscopically, non-symmetrical acoustic stream S1 and acoustic stream S2 (=S11) are produced in the liquid sample Ls contained in the reaction vessel 5.

Figure 10:
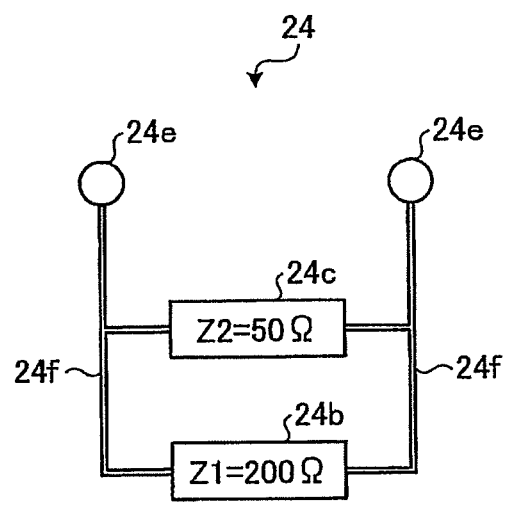
FIG. 10 is an equivalent circuit diagram in the case that the surface acoustic wave element in FIG. 7 is driven at the center frequency of the other sound generation section.

On the other hand, for example, when the drive control section 21 inputs a drive signal with frequency fc2 to the surface acoustic wave element 24, as shown in FIG. 10, the electric impedance of the sound generation section 24b becomes Z1=200 ohms, and the electric impedance of the sound generation section 24c becomes Z2=50 ohms, which is generally inverse to the previous case. For this reason, the sound generation section 24b of the surface acoustic wave element 24 is weakly excited, while the sound generation section 24c of the surface acoustic wave element 24 is strongly excited.

Figure 11:
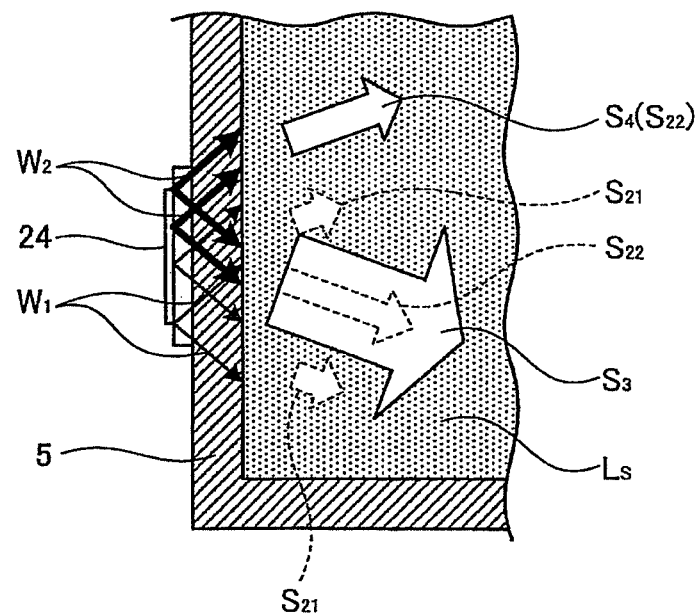
FIG. 11 is a partial cross sectional view of a reaction vessel for explaining sound waves which respective sound generation sections generate and acoustic streams caused in a liquid sample by the sound waves in the case of FIG. 10.

Therefore, since the sound generation sections 24b and 24c are formed so as to alternately arrange the origins of the acoustic streams, as shown in FIG. 11, the acoustic stream S22 which is produced toward the diagonally downward right direction in the liquid sample Ls of the acoustic stream S22 due to the sound wave W2 generated by the sound generation section 24c is produced at a location interleaved with two acoustic streams S21 produced toward the diagonally upward right direction and toward the diagonally downward left direction in the liquid sample Ls due to the sound wave W1 generated by the excited sound generation section 24b. Due to the above, two acoustic streams S21 are integrated with the acoustic stream S22 produced toward the diagonally downward right direction to form an acoustic stream. S3 with large cross section area and high flow speed. While the acoustic stream S22 produced toward the diagonally upward right direction in the liquid sample Ls due to the sound wave W2 generated by the excited sound generation section 24c is an independent flow which has smaller cross section area and lower flow speed compared with the acoustic stream S3. Therefore, when the surface acoustic wave element 24 is driven with drive frequency F=fc2, macroscopically, non-symmetrical acoustic stream S3 and acoustic stream S4 (=S22) are produced in the liquid sample Ls contained in the reaction vessel 5.

Figure 12:
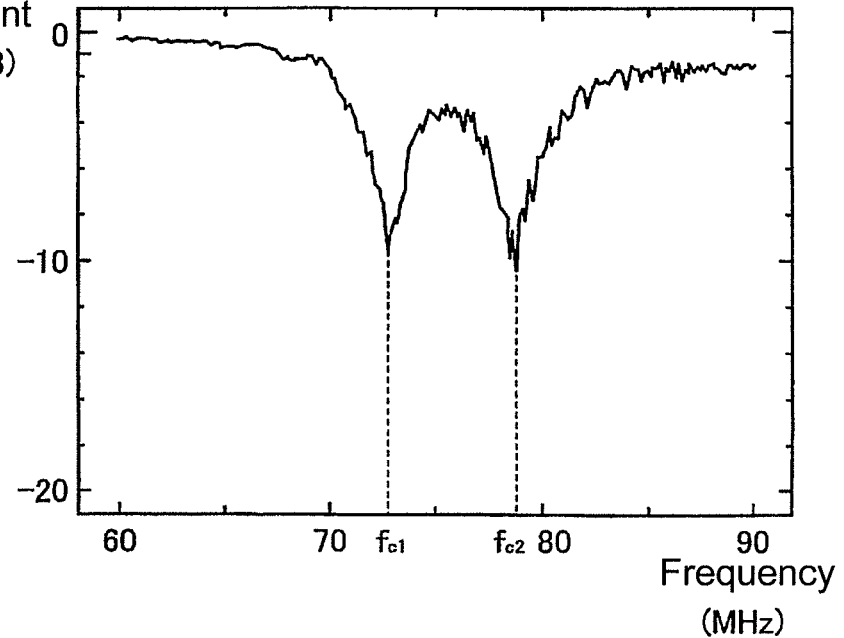
FIG. 12 is a frequency characteristic chart showing an example of center frequencies and input reflection coefficients that two sound generation sections which a surface acoustic wave element comprises have.

Here, ion exchanged water contained in the reaction vessel 5 was stirred by using the stirring device 20 with the surface acoustic wave element 24 having sound generation sections 24b, 24c of the frequency characteristic shown in FIG. 12 relating to center frequencies fc1 and fc2 and input reflection coefficient (dB). The flow speed distribution of the acoustic stream when driving the surface acoustic wave element 24 with drive frequency F=fc1 and the flow speed distribution of the acoustic stream when driving the surface acoustic wave element 24 with drive frequency F=fc2 are shown in FIG. 13, respectively.

FIG. 13 is a figure which visualizes the flow speed distribution (mm/s) in the ion exchanged water contained in the reaction vessel 5 with PIV when the surface acoustic wave element 24 is driven with center frequency fc1 (=78.3 MHz) and center frequency fc2 (=79.2 MHz), respectively, where vertical axis and horizontal axis are a distance (mm) in the upward direction along the side wall 5b and a distance (mm) in the direction perpendicular to the side wall 5b with the intersection line of inner surface of side wall 5b and an upper surface of bottom wall as reference line, to which the surface acoustic wave element 24 is mounted.

Here, θ denotes an angle which the acoustic stream makes to the perpendicular plane of the sidewall 5b. In addition, PIV is Particle Image Velocimetry, and generally, it is a method which adds an imaging process and an image analysis technology to a visualizing technology that makes visible a stream by adding markers such as tracers into an invisible stream to obtain simultaneous and multi-point velocity information of flow field.

While when the surface acoustic wave element 24 is driven with a drive frequency F=f1(<fc1) which is lower than a center frequency fc1 of the sound generation section 24b, the electric impedance of the sound generation section 24b becomes Z1=200 ohms, and the electric impedance of the sound generation section 24c becomes Z2=∞. For this reason, only the sound generation section 24b of the surface acoustic wave element 24 is weakly excited. Therefore, when the surface acoustic wave element 24 is driven with a drive frequency F=f1, macroscopically, symmetrical acoustic streams S5 and S6 with the smallest cross section area and low flow speed are produced in the liquid sample Ls contained in the reaction vessel 5.

When the surface acoustic wave element 24 is driven with the drive frequency F=f2 (fc1<f2<fc2) of intermediate frequency between the center frequency fc1 of the sound generation section 24b and the center frequency fc2 of the sound generation section 24c, the electrical impedances of the sound generation section 24b and the sound generation section 24c become Z1 and Z2=100 ohms. Therefore, the sound generation section 24b and the sound generation section 24c of the surface acoustic wave element 24 are excited generally in the same level with the intensity of the electrical impedance between 50 ohms and 200 ohms. For this reason, when the surface acoustic wave element 24 is driven with a drive frequency F=f2, macroscopically, symmetrical acoustic streams S7 and S8 are produced in the liquid sample Ls contained in the reaction vessel 5 with generally same flow speed as acoustic streams S5 and S6 but a slightly larger cross section area than S5 and S6.

While when the surface acoustic wave element 24 is driven with drive frequency F=f3 (>fc2) which is higher than the center frequency fc2 of the sound veneration section 24c, the electric impedance of the sound generation section 24b becomes Z1=∞, and the electric impedance of the sound generation section 24c becomes Z2=200 ohms. For this reason, only the sound generation section 24c of the surface acoustic wave element 24 is weakly excited. Therefore, when the surface acoustic wave element 24 is driven with a drive frequency F=f3, macroscopically, symmetrical acoustic stream S9 and S10 with the smallest cross section area and low flow speed are produced in the liquid sample Ls contained in the reaction vessel 5.

Figure 14:
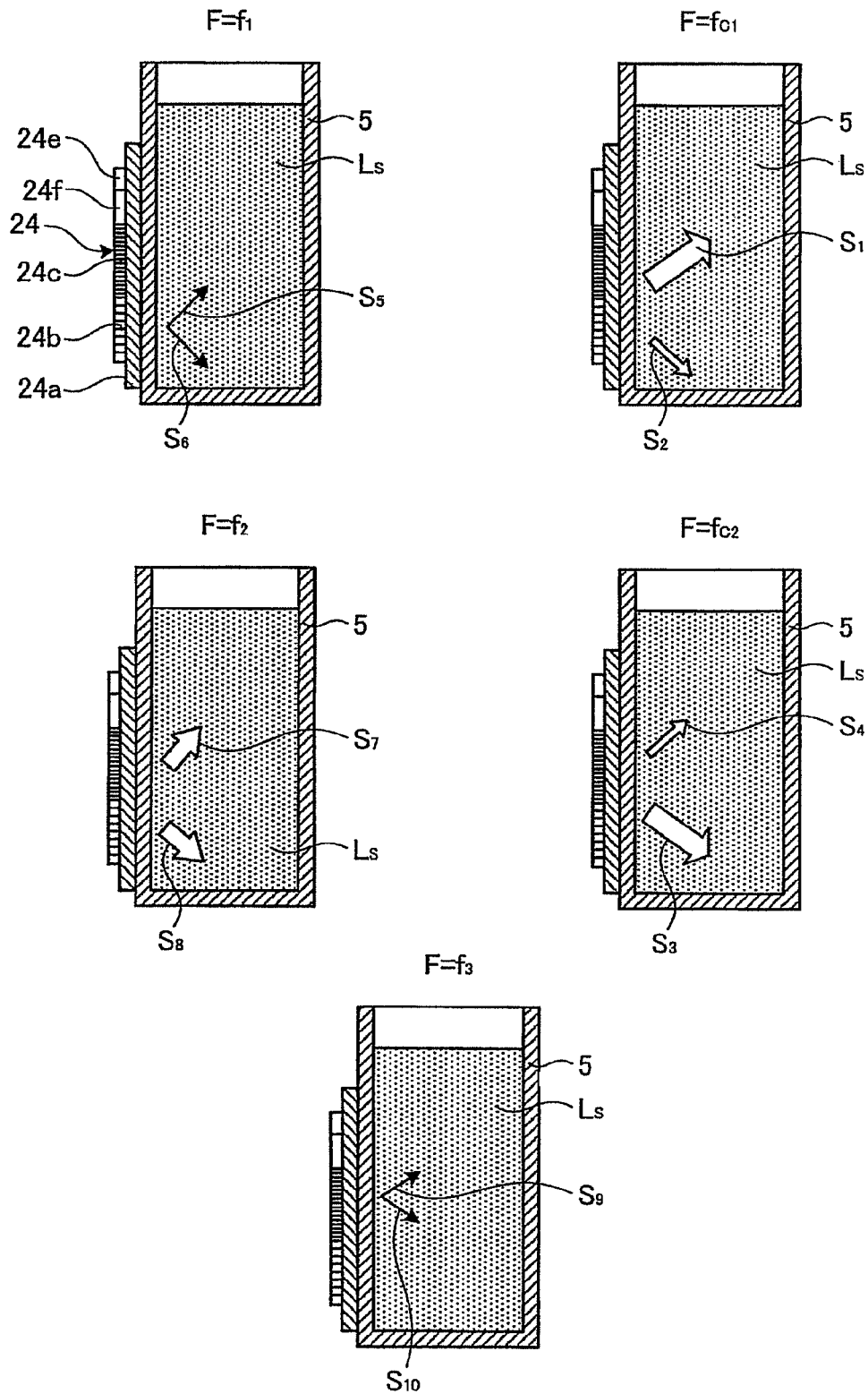
FIG. 14 is a figure indicating acoustic streams caused in a liquid sample contained in a reaction vessel for respective drive frequencies when driving a surface acoustic wave element of FIG. 4.

Therefore, when the respective acoustic stream produced in the liquid sample Ls contained in the reaction vessel are depicted for respective drive frequency F=f1, fc1, f2, fc2 and f3, FIG. 14 is obtained. In addition, if the electric impedance of an external electric system is other value, for example 70 ohms, the electric impedance at the center frequencies of the sound generation sections 24b and 24c may be designed to be 70 ohms.

Therefore, the automatic analyzing device 1 creates a combination of the drive frequency and the analyte and the reagent at which stirring becomes best, combination of the drive frequency and the amount of the liquid or combination thereof to store in the control section 15 by initially making a survey of stirring condition for a different drive frequency with a combination of the analyte and the reagent. Then, the control section 15 automatically selects the drive frequency of the stirring device 20 from the combination of an analyte and a reagent included in the analysis information input from a host computer and the like to output to the drive control circuit 23. Thereby the stirring device 20 can drive the surface acoustic wave element 24 with an optimized frequency for the combination of the analyte and the reagent.

For this purpose, the automatic analyzing device 1 switches a drive frequency of the drive signal which drives the surface acoustic wave element 24 by the drive control circuit 21, for example when the amount of the liquid sample retained in the reaction vessel 5 is small, to input the drive signal with frequency f1 to the surface acoustic wave element 24. In this case, only the sound generation section 24b of the surface acoustic wave element 24 of the stirring device 20 is weakly excited and the liquid sample is effectively stirred while suppressing energy consumption.

Figure 9:
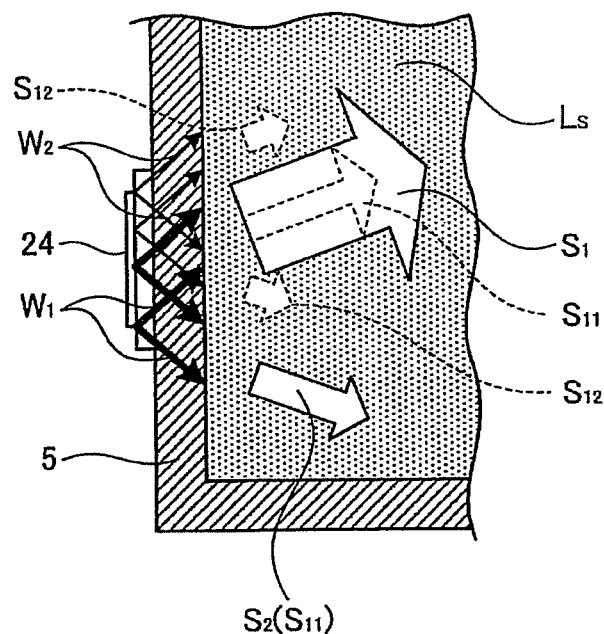
FIG. 9 is a partial cross sectional view of a reaction vessel for explaining sound waves which respective sound generation sections generate and an acoustic stream caused in a liquid sample by the sound waves in the case of FIG. 8.

On the other hand, when the amount of the liquid retained in the reaction vessel 5 is large, the automatic analyzer 1 inputs the drive signal with the frequency fc1 or the frequency fc2 to the surface acoustic wave element 24. In this case, the sound generation section 24b or the sound generation section 24c of the surface acoustic wave element 24 of the stirring device 20 is strongly excited. As a result, as shown in FIG. 9, FIG. 11 and FIG. 14, asymmetric acoustic streams S1 and S2 or acoustic streams S3 and S4 produce a stirring stream which largely rotates within the whole liquid sample Ls to stir the whole liquid sample Ls.

As described above, the stirring device 20 controls the drive frequency F within frequency band (f1 to f3) by the drive control section 21 so that the plurality of sound generation sections 24b and 24c simultaneously generate sound waves with different frequencies, to always drive one or more sound generation section to stir the liquid sample Ls retained in the reaction vessel 5 according to the amount of the liquid sample Ls. Therefore, since patterns of the generated acoustic streams become diversified compared to the conventional stirring device with surface acoustic wave elements in which resonant frequencies are not overlapped, which can increase stirring efficiency to reduce time required for stirring.

Figure 15:
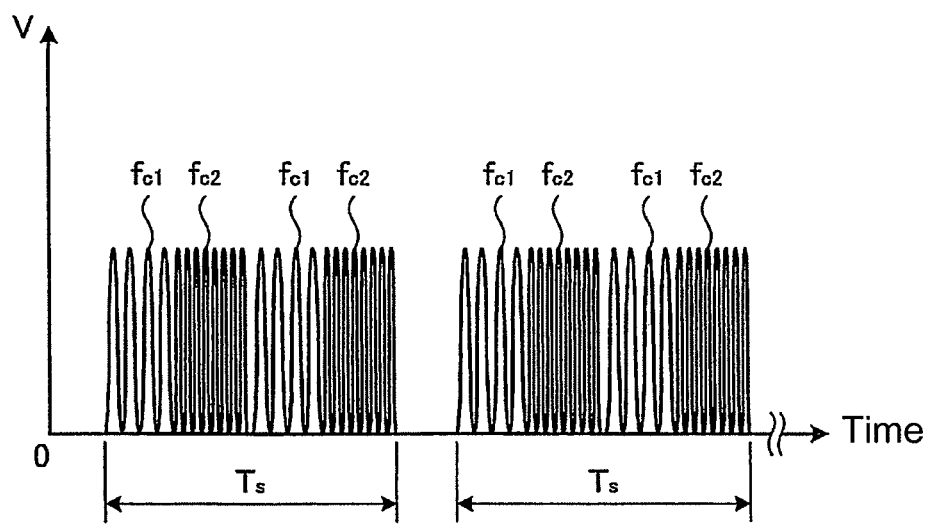
FIG. 15 is a waveform figure showing an example of a drive signal for driving a surface acoustic wave element.

In this case, the stirring device 20 may alternately vary the frequency of the drive signal input to the surface acoustic wave element 24, as shown in FIG. 15, within the stirring time Ts in a time-sharing manner between the frequency fc1 and the frequency fc2. Thus, the asymmetric acoustic streams S1 and S2 and the asymmetric acoustic streams S3 and S4 are alternately produced in the liquid sample Ls retained in the reaction vessel 5 to produce a stirring stream on a gas-liquid interface in addition to the bottom of the vessel; thereby the whole liquid sample Ls is stirred. The switching time of the frequencies fc1 and fc2 is not always set to 1:1. It may be appropriately changed according to the property of the liquid sample Ls such as viscosity or the amount of the liquid and the like.

In addition, the position of the sound generation section 24b and the sound generation section 24c of the surface acoustic wave element 24 may be exchanged. In such an arrangement, the surface acoustic wave element 24 can produce acoustic stream which has different distribution from that of the acoustic stream shown in FIG. 14.

Modified Example

Figure 16:
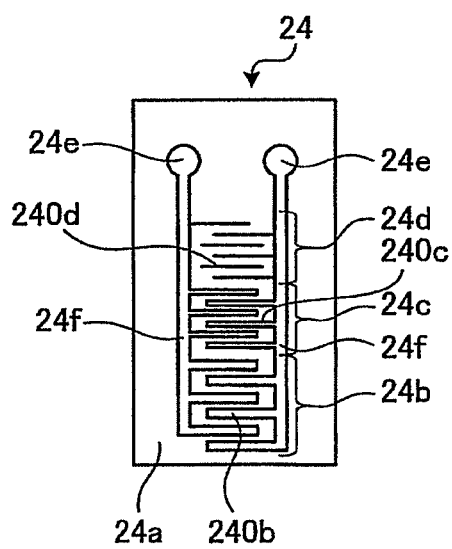
FIG. 16 is a front elevation view showing a modified example of a surface acoustic wave element configured stirring device.
Figure 17:
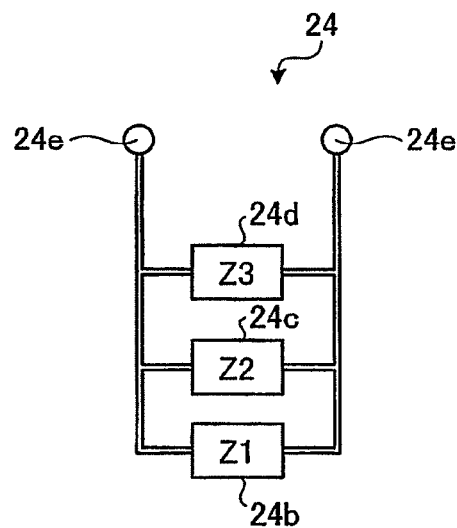
FIG. 17 is an equivalent circuit diagram of the surface acoustic wave element shown in FIG. 16.
Figure 18:
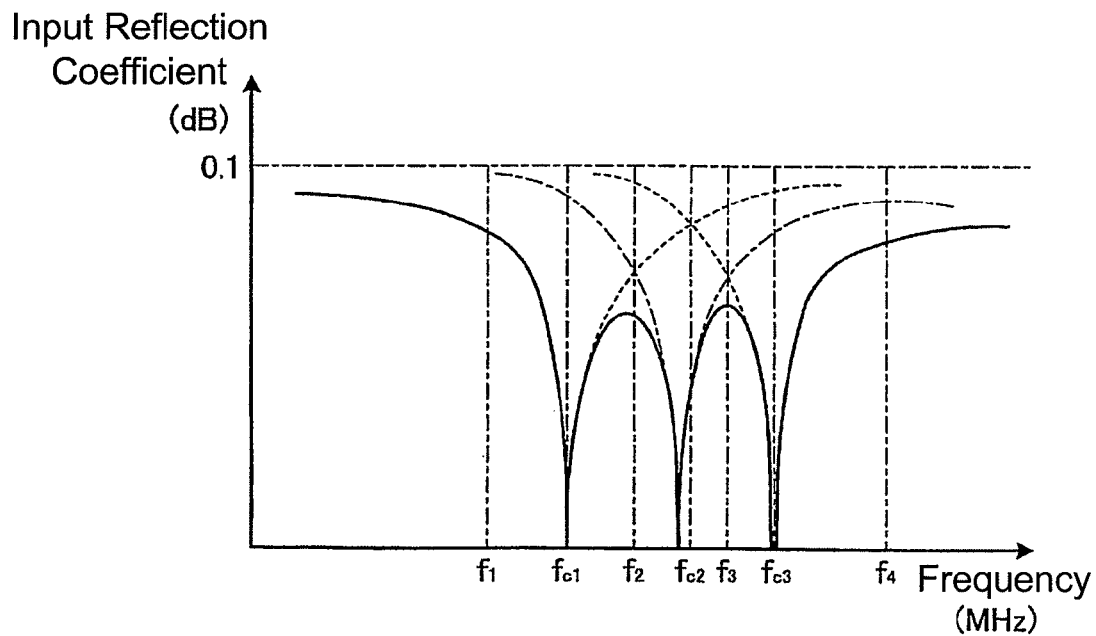
FIG. 18 is a frequency characteristic chart relating to center frequencies and input reflection coefficients which a sound generation section of a surface acoustic wave element shown in FIG. 16 has.

As shown in FIG. 16, a sound generation section 24d with the center frequency fc3 (fc1<fc2<fc3) (MHz) may be connected in parallel in addition to the sound generation sections 24b and 24c with the respective center frequencies fc1 and fc2. In this case, electric impedances of the sound generation sections 24b, 24c and 24d of the surface acoustic wave element 24 at respective center frequencies are designed to become 50 ohms which is the same as that of the external electric system. In addition, the equivalent circuit of the surface acoustic wave element 24 is as shown in FIG. 17 with the impedances of the sound generation sections 24b, 24c and 24d being defined as Z1 Z2 and Z3 respectively.

In this case, a part of resonant frequency bands of the sound generation sections 24b, 24c and 24d are overlapped. In addition, concerning an input reflection coefficient (dB), the sound generation sections 24b, 24c and 24d have frequency characteristics separately shown with dotted lines in FIG. 6, and a solid line shows a frequency characteristic in combination of three frequency characteristics. Furthermore, the adjacent sound generation sections 24b, 24c and the adjacent sound generation sections 24c, 24d of the surface acoustic wave element 24 are formed so that origins of acoustic streams are arranged alternately.

Figure 19:
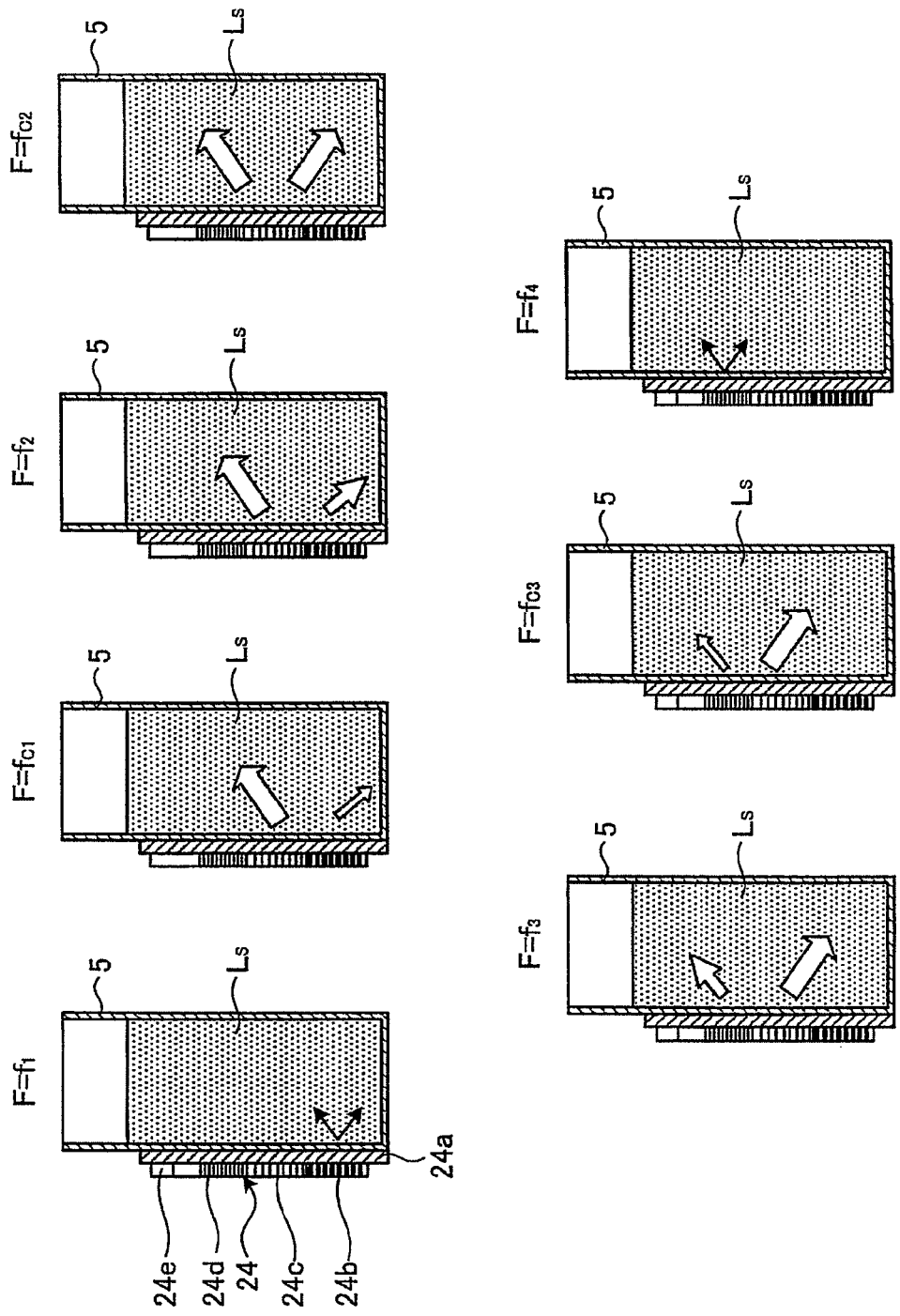
FIG. 19 is a figure indicating acoustic streams caused in a liquid sample contained in a reaction vessel for respective drive frequencies when driving a surface acoustic wave element as shown in FIG. 16.

Therefore, when the surface acoustic wave element 24 is driven, for example, with a drive frequency F=f1(<fc1) which is lower than the center frequency fc1 of the sound generation section 24b, only the sound the sound generation section 24b of the surface acoustic wave element 24 is weakly excited. Therefore, as shown with arrows in FIG. 19, macroscopically, symmetrical acoustic streams with the smallest cross section area and low flow speed are produced in the liquid sample Ls contained in the reaction vessel 5.

Next, when the surface acoustic wave element 24 is driven with the drive frequency F=fc1 which is a center frequency fc1 of the sound generation section 24b, as described in FIG. 9, the sound generation section 24b is strongly excited and the sound generation section 24c is weakly excited, while the sound generation section 24d is hardly excited. Therefore, macroscopically, as shown with arrows in FIG. 19, asymmetrical acoustic streams with increased cross section area and increased flow speed and dominant diagonally upward streams are produced in the liquid sample Ls contained in the reaction vessel 5.

Next, when the surface acoustic wave element 24 is driven with the drive frequency F=f2 (fc1<f2<fc2) of intermediate frequency between the center frequency fc1 of the sound generation section 24b and the center frequency fc2 of the sound generation section 24c, the sound generation sections 24b and 24c are excited in the same intensity, and the sound generation section 24d is weakly excited. Therefore, macroscopically, as shown with arrows in FIG. 19, diagonally upward acoustic stream slightly shifted upwardly compared to that of drive frequency F=fc1 is produced and diagonally downward acoustic stream with increased cross section area is produced in the liquid sample Ls contained in the reaction vessel 5.

In addition, when the surface acoustic wave element 24 is driven with the drive frequency F=fc2 which is the center frequency fc2 of the sound generation section 24c, the sound generation section 24c is strongly excited and the sound generation sections 24b and 24d are excited at the same intensity but weaker than that of the sound generation section 24c. Therefore, macroscopically, as shown with arrows in FIG. 19, symmetric streams of a diagonally upward direction and a diagonally downward direction are produced in the liquid sample Ls contained in the reaction vessel 5.

Next, when the surface acoustic wave element 24 is driven with the drive frequency F=f3 (fc2<f3<fc3) which is an intermediate frequency between the center frequency fc2 of the sound generation section 24c and the center frequency fc3 of the sound generation section 24d, the sound generation sections 24c and 24d are excited in the same intensity, while the oscillation of the sound generation section 24c is weaker than those of the sound generation sections 24c and 24d. Therefore, macroscopically, as shown with arrows in FIG. 19, the streams in which a diagonally downward stream is more dominant than a diagonally upward stream are produced in the liquid sample Ls contained in the reaction vessel 5.

Next, when the surface acoustic wave element 24 is driven with the drive frequency F=fc3 which is a center frequency fc3 of the sound generation section 24d, the sound generation section 24d is strongly excited and the sound generation section 24c is weakly excited, while the sound generation section 24b is hardly excited. Therefore, macroscopically, as shown with arrows in FIG. 19, the streams in which a diagonally downward stream is more dominant than a diagonally upward stream are produced in the liquid sample Ls contained in the reaction vessel 5. At this time, the diagonally downward stream is slightly shifted upward compared to the case of the drive frequency F=f3.

And then, when the surface acoustic wave element 24 is driven with the drive frequency F=f4 (>fc3) which exceeds the center frequency fc3 of the sound generation section 24d, only the sound generation section 24d is weakly excited. Therefore, macroscopically, as shown with arrows in FIG. 19, symmetrical acoustic streams with the smallest cross section area and low flow speed are produced from the vicinity of the sound generation section 24d in the liquid sample Ls contained in the reaction vessel 5.

As described above, as is apparent by comparing FIG. 14 and FIG. 19, by adding the sound generation section 24d, the acoustic stream produced in the liquid sample Ls of the surface acoustic wave element 24 becomes complex. Therefore, when using the surface acoustic wave element 24 added with the sound generation section 24d, the stirring device 20 can generate various acoustic streams in the liquid sample retained in the reaction vessel 5 by changing frequencies as appropriate to drive the surface acoustic wave element 24, the liquid sample is effectively stirred according to the amount of liquid while suppressing excess energy consumption thereby reducing time required for a stirring.

Figure 20:
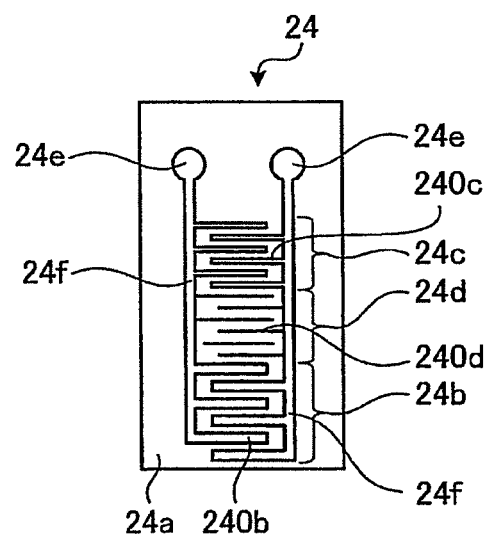
FIG. 20 is a front elevation view showing a modified example of a surface acoustic wave element as shown in FIG. 16.
Figure 21:
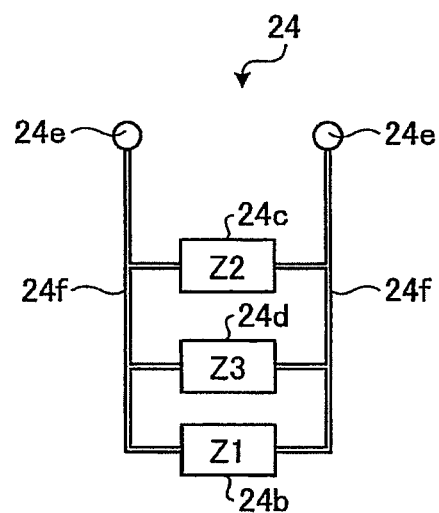
FIG. 21 is an equivalent circuit diagram of a surface acoustic wave element as shown in FIG. 20.

In this case, as shown in FIG. 20, the sound generation section 24d may be located between the sound generation section 24b and the sound generation section 24c of the surface acoustic wave element 24. The equivalent circuit of the surface acoustic wave element 24 is depicted in FIG. 21, where Z1, Z2 and Z3 indicate the electric impedances of the sound generation sections 24b, 24c and 24d, respectively.

Figure 22:
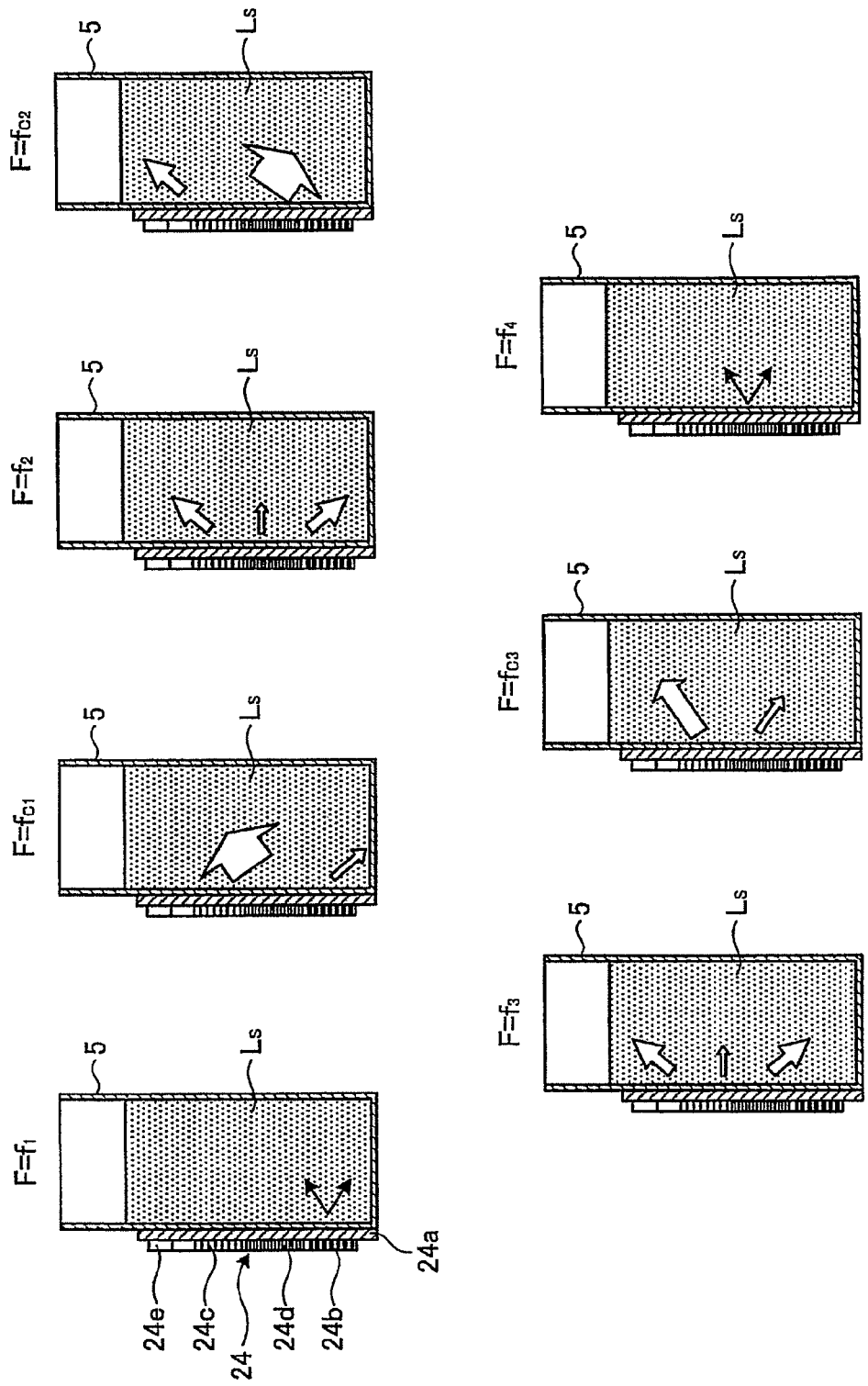
FIG. 22 is a figure indicating acoustic streams caused in a liquid sample retained in a reaction vessel for respective drive frequencies when driving a surface acoustic wave element as shown in FIG. 20.

In this case, according to the above description, the respective acoustic streams produced in the liquid sample Ls retained in the reaction vessel 5 are shown with arrows in FIG. 22 for respective drive frequencies F=f1, fc1, f2, fc2, f3, fc3 and fc4. As is apparent by comparing the acoustic streams indicated in FIG. 22 with the acoustic stream indicated in FIG. 19, the acoustic streams produced in the liquid sample Ls are further varied by changing the arrangement of the sound generation sections 24b, 24c and 24d. Therefore, when using the surface acoustic wave element 24 in which the sound generation sections 24b, 24c and 24d are thus arranged, by changing frequencies as appropriate to drive the surface acoustic wave element 24, the stirring device 20 can effectively stir the liquid sample according to the amount of the liquid while suppressing excess energy consumption thereby reducing time required for a stirring.

Figure 23:
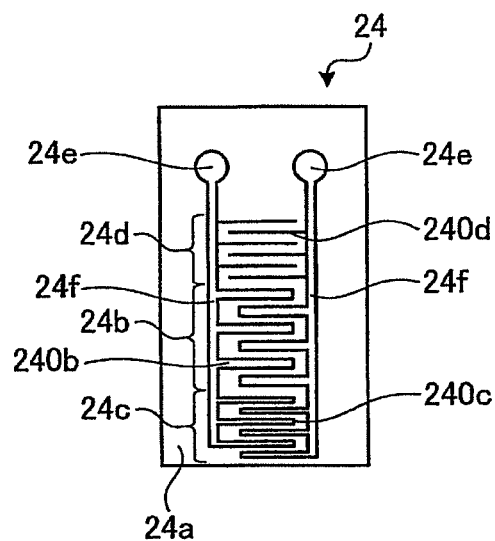
FIG. 23 is a front elevation view showing another modified example of a surface acoustic wave element as shown in FIG. 16.
Figure 24:
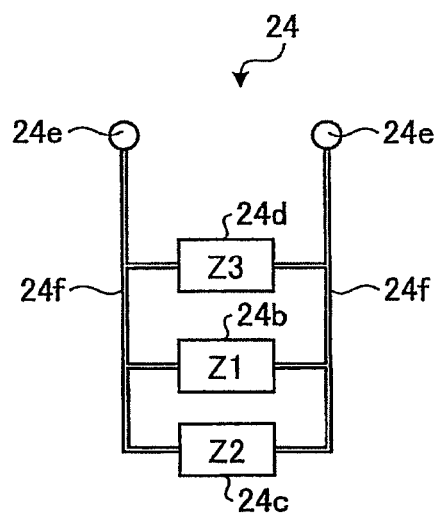
FIG. 24 is an equivalent circuit diagram of a surface acoustic wave element as shown in FIG. 23.

Therefore, as shown in FIG. 23, the sound generation section 24b may be located between the sound generation section 24c and the sound generation section 24d of the surface acoustic wave element 24. In this case, the equivalent circuit of the surface acoustic wave element 24 is depicted in FIG. 24, where Z1, Z2 and Z3 indicate the electric impedances of the sound generation sections 24b, 24c and 24d, respectively.

Figure 25:
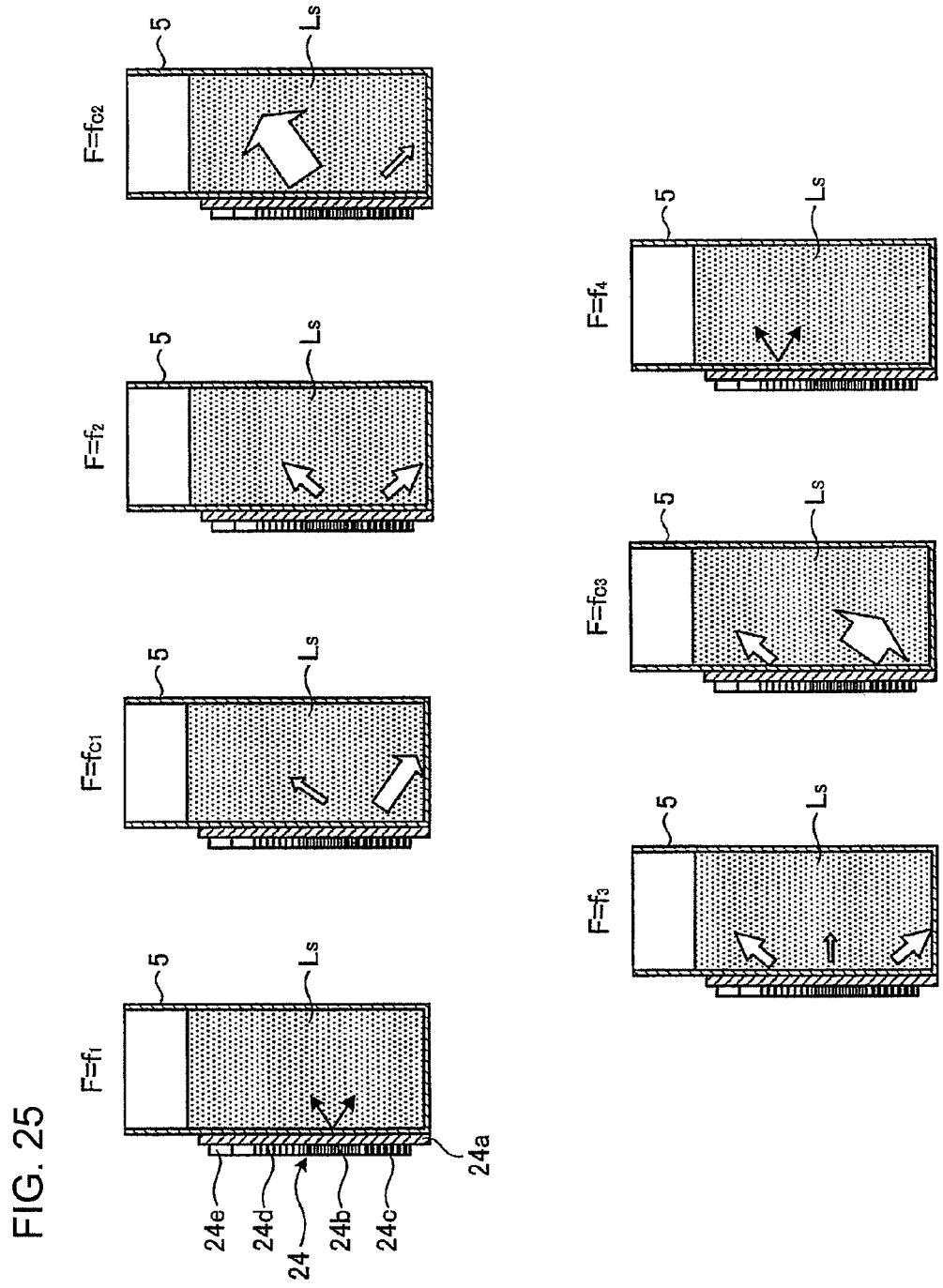
FIG. 25 is a figure indicating acoustic streams caused in a liquid sample contained in a reaction vessel for respective drive frequencies when driving a surface acoustic wave element as shown in FIG. 23.

In this case, the respective acoustic streams produced in the liquid sample Ls retained in the reaction vessel 5 are shown with arrows in FIG. 25 for respective drive frequencies F=f1, fc1, f2, fc2, f3, fc3 and f4. Therefore, when using the surface acoustic wave element 24 in which the sound generation sections 24b, 24c and 24d are thus arranged, in the stirring device 20, a different acoustic stream for each drive frequency is produced in the liquid sample Ls in the reaction vessel 5, the stirring device 20 can effectively stir the liquid sample according to the amount of the liquid while suppressing excess energy consumption thereby reducing time required for a stirring.

Here, the stirring device 20 using the surface acoustic wave element 24 having the sound generation sections 24b, 24c and 24d may vary the frequency of the drive signal input to the surface acoustic wave element 24 by time-sharing within stirring time to the drive frequency F=fc1, fc2 and fc3 alternately.

In addition, in the stirring device 20 using the surface acoustic wave element 24 having the sound generation sections 24b, and 24c, the drive frequency F may be slid and varied between frequencies f1 and f3 in the stirring time, and in the stirring device 20 using the surface acoustic wave element 24 having the sound generation sections 24b, 24c and 24d, the drive frequency F may be slid and varied between frequencies f1 and f4 in the stirring time.

Figure 26:
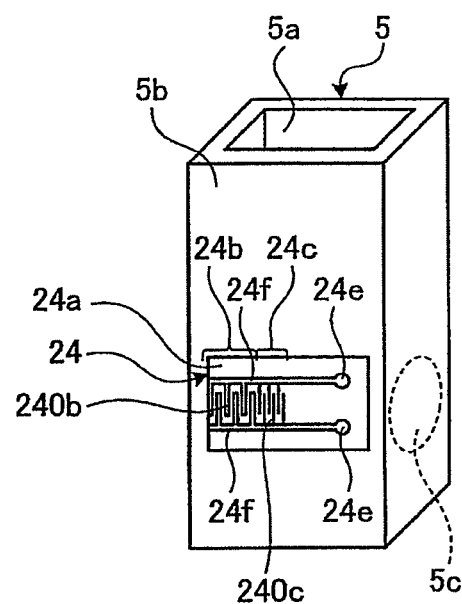
FIG. 26 is a perspective view depicting another mounting arrangement for mounting a surface acoustic wave element to a reaction vessel.
Figure 27:
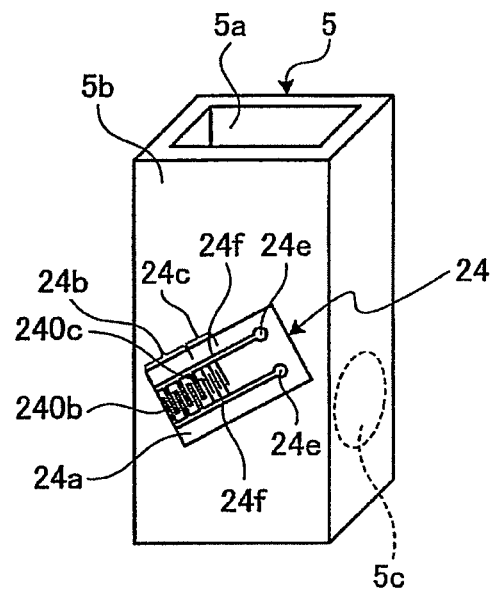
FIG. 27 is a perspective view depicting yet another mounting arrangement for mounting a surface acoustic wave element to a reaction vessel.

The various surface acoustic wave elements 24 as explained above may be mounted on the sidewall 5b of the reaction vessel 5 with a longitudinal direction of the piezoelectric substrate 24a directed to the width direction of the sidewall 5b as shown in FIG. 26. In such mounting, the stirring device 20 can produce different acoustic streams including horizontal flow for each drive frequency. Therefore, as shown in FIG. 27, when the various surface acoustic wave elements 24 as explained above are mounted on the side wall 5b of the reaction vessel 5 with a longitudinal direction of the piezoelectric substrate 24a tilting against the width direction of the side wall 5b, different acoustic streams including a horizontal direction component and a vertical direction component for each drive frequency can be produced.

Figure 28:
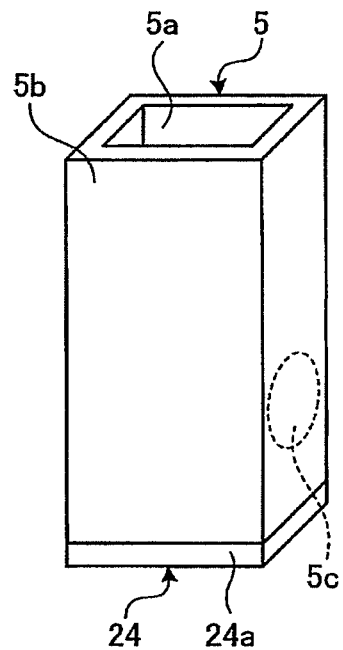
FIG. 28 is a perspective view depicting amounting arrangement for mounting a surface acoustic wave element on the bottom surface of a reaction vessel.

Furthermore, as shown in FIG. 28, the various surface acoustic wave elements 24 as explained above may be mounted on the bottom face of the reaction vessel 5. In this case, the surface acoustic wave element 24 can be mounted with the longitudinal direction of the piezoelectric substrate 24a being directed to various directions taking the direction of the acoustic streams to be generated into account.

In addition, the reaction vessel to which various surface acoustic wave elements 24 as explained above is mounted may be cylindrical shape instead of the square cylindrical shaped reaction vessel 5.

In addition, the various surface acoustic wave elements 24 as described above may be driven wirelessly and the liquid sample retained in the reaction vessel 5 may be stirred using surface acoustic wave in addition to bulk wave.

Figure 29:
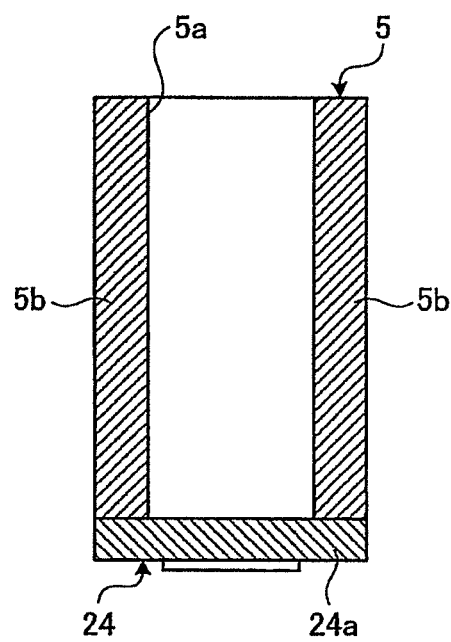
FIG. 29 is a perspective view depicting amounting arrangement for mounting a surface acoustic wave element which also serves as a bottom surface of the reaction vessel.

Furthermore, as shown in FIG. 29, the surface acoustic wave element 24 may serve as the bottom face of the reaction vessel 5.

In addition, in the surface acoustic wave element 24 described above, a plurality of sound generation sections are formed on a single piezoelectric substrate 24a; however, these sound generation sections are not required to be formed on the single piezoelectric substrate 24a, instead, they may be formed so far as a plurality of the sound generation sections are electrically connected in parallel, and center frequencies of respective fundamental waves of sound generation sections differ from each other, respective resonant frequency bands of the sound generation section are partially overlapped with each other, and origins of acoustic streams caused by sound wave radiated to the vessel from different sound generation section are located alternately. In addition, according to use, shape or arrangement (dimension, location and the like) of a plurality of sound generation sections may be optimized as appropriate.

INDUSTRIAL APPLICABILITY

As described above, the stirring device and the analyzing device of the present invention are useful to reduce time required for stirring, especially suitable for increasing stirring efficiency per time unit.

The invention claimed is:

1. A stirring device for stirring a liquid retained in a vessel with a sound wave characterized by comprising:

a sound wave generation means including sound generation sections located on a piezoelectric substrate, the sound generation means being configured so that a plurality of the sound generation sections are electrically connected in parallel, and center frequencies of respective fundamental waves of the sound generation sections differ from each other, respective resonant frequency bands of the sound generation sections are partially overlapped with each other, and origins of an acoustic stream caused by sound waves radiated to the vessel from different sound generation sections are located alternately; and a drive control circuit programmed to control a frequency of a drive signal input to the sound wave generation means so that at least two sound generation sections of the plurality of sound generation sections generate sound waves simultaneously, wherein the drive control circuit is further programmed to vary the frequency of the drive signal so that the drive signal is input to the sound wave generation means at two or more different frequencies, each frequency strongly exciting and weakly exciting different subsets of the at least two sound generation sections.

2. The stirring device according to claim 1, wherein the drive control circuit is further programmed to vary a frequency of the drive signal input to the sound wave generation means based on an analysis item of the liquid and information of property or a liquid volume of the liquid.

3. The stirring device according to claim 1, wherein the drive control circuit is further programmed to vary a frequency of the drive signal to cause an acoustic stream which rotates in the liquid.

4. An analyzing device which stirs a liquid sample containing analyte and reagent retained in a vessel to be reacted to analyze the reacted liquid, characterized by comprising the stirring device according to claim 1.

5. The stirring device according to claim 1, wherein the sound generation sections have different circuit patterns.

\* \* \* \* \*